United States Patent
D'Alelio

[11] 3,979,406
[45] Sept. 7, 1976

[54] POLYMERIZABLE ESTERS CONTAINING OXAZOLIDINONE STRUCTURES

[76] Inventor: Gaetano D'Alelio, 2011 E. Cedar St., South Bend, Ind. 46617

[22] Filed: Jan. 2, 1975

[21] Appl. No.: 538,173

Related U.S. Application Data

[63] Continuation-in-part of Ser. No. 325,921, Jan. 22, 1973, abandoned, which is a continuation-in-part of Ser. No. 150,812, June 7, 1971, abandoned, which is a continuation of Ser. No. 778,826, Nov. 25, 1968, abandoned.

[52] U.S. Cl. .................. 260/307 C; 260/240 R; 260/240 G; 260/88.3 R; 526/23; 526/46; 526/260; 526/227
[51] Int. Cl.² ............................. C07D 263/06
[58] Field of Search ..................... 260/307 C

[56] References Cited
UNITED STATES PATENTS

| | | | |
|---|---|---|---|
| 3,313,747 | 4/1967 | Schramm | 260/2.5 |
| 3,519,608 | 7/1970 | Kelley | 260/86.1 |

*Primary Examiner*—Nicholas S. Rizzo
*Assistant Examiner*—Jose Tovar
*Attorney, Agent, or Firm*—Walter J. Monacelli

[57] ABSTRACT

Crosslinkable monomers containing oxazolidinone structures are prepared by reacting polyisocyanates with acrylic esters containing an epoxy group. These polyfunctional monomers can be homopolymerized or copolymerized with other monomers or polymers containing olefinic unsaturation to insoluble, infusible polymers, including copolymers. The monomers and polymers find utility as castings, moldings, impregnants, coatings and for the production of reinforced laminates. Curing can be accomplished by any of the known methods, such as thermally, by the use of catalysts, by ultraviolet light, and by ionizing radiation. The monomers have the formula

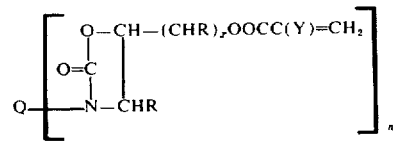

wherein $n$ has a numerical value of at least two, $x$ is 1–8, $R$ is hydrocarbon, $Y$ is H, $CH_3$ or CH, and $Q$ is a polyvalent organic moiety.

10 Claims, No Drawings

POLYMERIZABLE ESTERS CONTAINING OXAZOLIDINONE STRUCTURES

This application is a continuation-in-part of copending application Ser. No. 325,921, filed Jan. 22, 1973, which in turn is a continuation-in-part of application Ser. No. 150,812, filed June 7, 1971, which is a continuation of application Ser. No. 778,826, filed Nov. 25, 1968, all now abandoned.

The present invention relates to new crosslinkable monomers containing 2-oxazolidinone structures obtained by reacting a polyisocyanate with at least two moles of an acrylic ester containing an epoxy group.

The term "polyisocyanate" refers to a compound containing two or more isocyanate, (—NCO), groups. The term "epoxy" or "epoxide" refers to the oxirane structure,

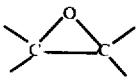

The term "2-oxazolidinone" refers to the structure

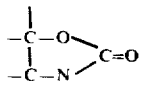

formed by the reaction of the oxirane moiety with the isocyanate moiety, thus

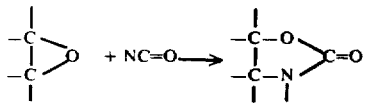

Glycidyl acrylate,

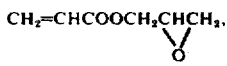

is a typical epoxy containing acrylic ester suitable for the production of the crosslinkable monomers of this invention, which on reaction with a polyisocyanate, $Q(NCO)_n$, yields a polyoxazolidinone containing terminal polymerizable $CH_2=C<$ groups, thus:

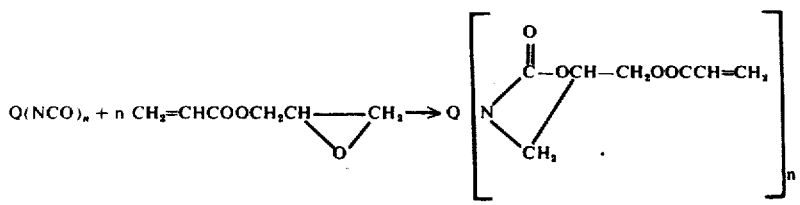

Most important is the fact that the vinyl group in the acrylic moiety is conjugated.

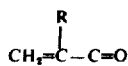

which makes it extremely reactive toward addition reactions, such as isocyanate has a tendency to perform. The chemistry of isocyanate addition reactions is well known.

While it might be expected that the isocyanate will reaction with the epoxide, it might be predicted that there would also be a reaction between the isocyanate and the conjugated acrylic structure. In this regard, Professor Henry Gilman, Editor-in-Chief, in *Organic Chemistry, An advanced Treatise*, John Wiley & Sons, Vol. 1, Second Edition, Seventh Printing, November 1949, Page 505, states: "Compounds having terminal unsaturated linkages may be classified as (1) terminal or nor-terminal cumulated unsaturated systems; (2) conjugated systems and (3) systems having the unsaturated linkages separated by one or more carbon atoms. Systems having terminal cumulated unsaturation comprise types like ketenes ($R_2C=C=O$), isocyanates ($RN=C=O$), isothiocyanates ($RN=C=S$) and thionylamines ($RN=S=O$).

In such systems, addition takes place predominantly, if not exclusively, under moderate conditions to the terminal unsaturated linkage." Gilman demonstrates this addition by reaction with a Grignard reagent as published in Journal of the American Chemical Society, 49, 236 (1927).

This type of reactivity in isocyanates was observed as early as 1904, when it was shown in Berichte, 37, 4627 (1904) that phenylisocyanate reacts with such molecules as acetyl.acetone, acetoacetic ester and malonic esters, whose anolized form contain the conjugated structures, $=C-CH=C-$, to give C-carbanilide derivatives. In view of the facts in these references, it would be expected that the conjugated acrylic structure would be reacted upon by the isocyanate and it is entirely unexpected that the conjugated acrylic structure would be left intact while isocyanate groups are being reacted with the epoxy group.

The surprising and unexpected feature of the present process is not that an epoxy group reacts with an isocyanate group to form the 2-oxazolidinone structure. The surprising discovery is that the vinyl group of the acrylic compound, which is in fact conjugated and made extremely active by the juxtaposition of the carbonyl group,

does not also react with the isocyanate group.

The polyisocyanates suitable for the practice of this invention are those corresponding to the formula $Q(NCO)_n$ wherein $n$ is at least 2 and Q is the polyvalent organic residue of the polyisocyanate. The $Q(NCO)_n$ compounds include non-polymeric as well as polymeric compounds, particularly the so-called prepolymers end-capped by —NCO groups developed for the commercially important polyurethane chemistry. In addition to the N, C and O atoms in the NCO groups of the $Q(NCO)_n$ compounds, these compounds can contain not only C and H atoms in the Q residue, but also O, N, S, halogen, silicon, titanium, phosphorus, and the like atoms in the Q moiety. In other words, the polyisocyanates can also have attached thereto groups other than isocyanates. Preferably such other groups are not reactive with the epoxy and acrylic groups. However where such other groups are reactive, sufficient of the epoxy-acrylic compound is used to compensate for such side reaction, or in other words to provide enough of such compound to react with such other groups and to have enough left over to react according to the process of this invention to produce the 2-oxazolidinone structures.

Preferably the polyisocyanate reactants corresponding to the formula $Q(NCO)_n$ are those in which Q is the hydrocarbon or substituted hydrocarbon residue of a polyisocyanate, such as alkylene, substituted alkylene, including cycloalkylene, and arylene or substituted arylene radical. In such cases, Q represents a hydrocarbon or substituted hydrocarbon radical having at least two valencies for attachment to —NCO, preferably of 2–20 carbon atoms.

Q is the residual organic moiety of the polyisocyanate and is preferably hydrocarbon but can also comprise radicals such as —Q'ZQ'— where Z is a divalent moiety such as —O—, —O—Q'—O—, —CO—, —CO$_2$—, —S—, —S—Q'—S—, —SO$_2$—, —NHC(O)O—, —N=CH—,

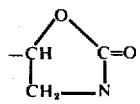

$RP(O)<$, $RP(S)<$, $RP<$, $R_2Si<$, and $R_2S(O)_2<$, and the like, and Q' is a smaller residue of the Q type, preferably hydrocarbon.

In summary Q is preferably a polyvalent organic moiety of 2–83 carbon atoms consisting of alkylene, phenylene, xylylene, tolylene, naphthylene hydrocarbon radicals or chloro derivatives thereof in which the chloridine atoms are attached directly to an aromatic nucleus, or derivatives thereof in which the derivative groups are connecting groups between two or more of said hydrocarbon radicals or said chloro derivatives, said connecting groups being selected from the class consisting of —O—, —C(O)—, —C(O)O—, —S—, —S(O)—, —S(O)$_2$—, —NHC(O)O—, —N=CH—,

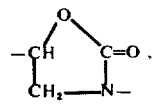

$RP(O)<$, $RP(S)<$, $RP<$, $R_2Si<$ and $R_2S(O)_2<$.

Examples of such compounds include hexamethylene diisocyanate, xylylene diisocyanates, (OCNCH$_2$CH$_2$C-H$_2$OCH$_2$)$_2$, 1-methyl-2,4-diisocyanatocyclohexane, phenylene diisocyanates, tolylene diisocyanates, chloro-phenylene diisocyanates, polyhalophenylene diisocyanates, such as poly(dichlorophenylene) diisocyanate, diphenylmethane-4,4'-diisocyanate, naphthalene-1,5-diisocyanate, triphenylmethane-4,4',4''-triisocyanate, xylene-α,α'-diisothiocyanate, isopropylbenzene-α,4-diisocyanate, OCN—C$_6$H$_4$OC$_6$H$_4$—NCO; OCN—C$_6$H$_4$OC$_6$H$_4$OC$_6$H$_4$NCO: OCN—C$_6$H$_4$C(O)C$_6$H$_4$NCO; OCNCH$_2$CH$_2$(OCH$_2$CH$_2$)$_{10}$OCH$_2$CH$_2$NCO; OCN—C$_6$H$_4$C(O)OC$_6$H$_4$NCO; OCNCH$_2$CH-C(O)OCH$_2$CH$_2$NCO;. OCN—C$_6$H$_4$SC$_6$H$_4$SC$_6$H$_4$NCO; OCN—C$_6$H$_4$SO$_2$C$_6$H$_4$NCO; OCNCH$_2$CH$_2$SCH$_2$CH$_2$SCH$_2$CH$_2$NCO; and the like.

Further included among the polyisocyanate reactants are dimers and trimers of isocyanates and diisocyanates and polymeric diisocyanates of the general formula $(QNCO)_n$ and $[Q(NCO)_n]_{n'}$ in which $n$ and $n'$ are two or more, as well as compounds of the general formula $M(NCG)_n$ in which $n$ is two or more and M is a monofunctional or polyfunctional atom or group and G represents oxygen or sulfur. Examples of this type include ethylphosphonic diisocyanate, $C_2H_5P(O)(NCO)_2$; and the corresponding thio compound, $C_2H_5P(S)(NCS)_2$; phenylphosphonic diisocyanate, $C_6H_5P(NCO)_2$; compounds containing a ≡Si—NCO group, such as $(C_2H_5)_2Si(NCO)_2$; isocyanates derived from sulfonamides, $R(SO_2NCO)_2$, such as $(C_6H_5)_2SO_2(NCO)_2$ and the like. Further included among the polyisocyanates are the isocyanate prepolymers, many of which are commercially available for current use in the preparation of polyurethane products. These prepolymers are prepared, as is well known, by end-capping polyols, such as polyethylene oxide, polybutylene oxide, etc. with diisocyanates, 1 mole of diisocyanate being used per hydroxyl group, in the presence of a catalyst, usually an organic stannate derivative.

A particularly useful mixture of polyisocyanates are the products obtainable by phosgenation of the reaction products of aniline and formaldehyde as expressed by the following general formula:

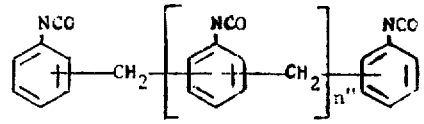

wherein $n''$ equals 0 to 10 or more.

Additional examples of suitable polyisocyanates are given in U.S. Pat. Nos. 3,367,992; 3,334,110; 3,415,901; 3,440,230 and 3,458,527; which examples of polysiocyanates are incorporated herein by reference.

All of these polyisocyanates have a plurality of isocyanate moieties attached to an organic residue represented as Q. Thus the polyisocyanates are represented by the formula $Q(NCO)_n$.

The acrylic esters suitable for the practice of this invention are those represented by the formula

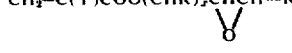

wherein Y represents H, CH$_3$ and CN, R represents H or a hydrocarbon containing one to 10 carbon atoms and $x$ has a numerical value of 1 to 8. While the hydrocarbon group R can represent less practical groups such as acetyleneic and spiro radicals, the hydrocarbon groups are preferably alkyl, including cycloalkyl, or aryl.

Typical examples of these acrylic esters are the commercially available glycidyl esters,

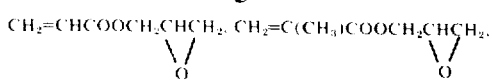

as well as those esters which are synthesized by the reaction of $CH_2=C(Y)COCl$ and epoxy alcohols

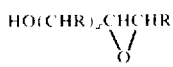

in the presence of a hydrohalide acceptor such as tertiary amines, for examples,

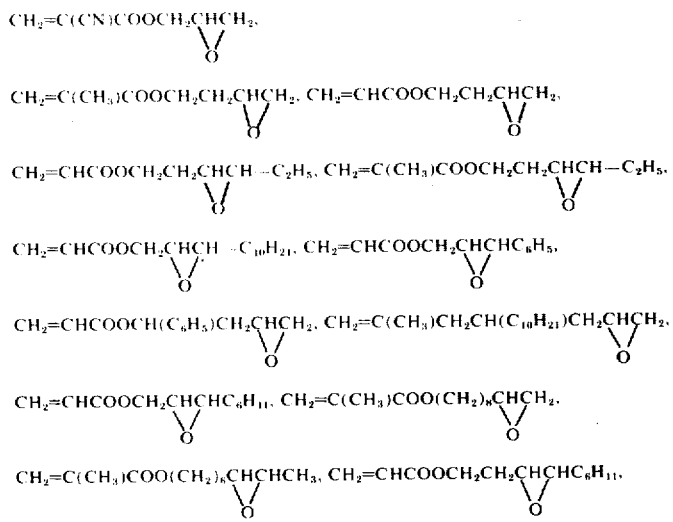

etc.

The uncatalyzed reactions between the polyisocyanates and the epoxy-containing acrylic esters are relatively slow and sluggish but proceed more readily in the range of 0° to 150° C., preferably 10°–120° C., in the presence of catalytic quantities, e.g. at least 0.01, preferably at least 0.1 percent by weight of a tertiary amine, $R'_3N$, or of a quaternary ammonium halide, $R'_4NX$, wherein $R'$ represents a hydrocarbon radical or a derivative thereof in which the derivative group may be hydroxy, epoxy, etc., including groups which might react with the isocyanates and thereby become part of the monomer or polymer. Two of the $R'$ groups may be jointed to form a cyclic amine such as pyridine, quinoline, isoquinoline, N-methylmorpholine, etc., and also triethylamine, tributylamine, dimethylaniline, triethylene diamine, tris(dimethyl amino-methyl)phenol, tetramethylammonium chloride, tetramethylammonium bromide, methylpyridinum bromide, benzyltrimethylammonium bromide, etc. Preferably the tertiary amine or quaternary ammonium halide is one in which the residue, that is the portion other than nitrogen or halogen, is hydrocarbon, however, other substituent groups which will not interfere with the purpose of the amine can be present.

As co-catalysts with the tertiary amines or the quaternary ammonium halides, catalytic quantities of primary and secondary alcohols containing one to six carbon atoms are particularly useful, such as methyl, ethyl, propyl, isopropyl, butyl, hexyl alcohol, etc.

In the reaction with a polyisocyanate, at least 2 moles of the acrylic esters containing an epoxy group are used. Thus, when the polyisocyanate is a triisocyanate, the reaction is performed with at least 2 moles of the acrylic ester leaving one isocyanate function unreacted, or three moles of ester can be used to convert the three isocyanate groups to oxazolidinone structure. Furthermore, the amount of the acrylic ester used can be greater than that required to react with the number of isocyanate groups present in the polyisocyanate, since any excess used can be left admixed with the polyoxazolidinone and copolymerized therewith.

Since the acrylic esters used in preparing the new monomers of this invention and the products of this invention are active polymerizable monomers, the reaction is performed preferably in an inert atmosphere and preferably in the presence of a polymerization inhibitor to retard or prevent polymerization through the vinyl structure of the acrylic ester. As a polymerization inhibitor, any of the well known inhibitors for vinyl type polymerizations can be used such as hydroquinone, tertiarybutyl catechol, 2,6-ditertiarybutyl phenol, phenol, cresols, xylenols, nitrophenols, naphthyl amine, copper acetate, catechol, resorcinol, methoxyphenols, dimethylaminophenols, nitromethane, etc. Tertiarybutyl catechol and 2,6-ditertiary cresol are preferred.

The new monomers of this invention are polymerized to thermosetting polymers by any of the techniques well known in the art for the polymerization of vinyl-type monomers. They can be polymerized or copolymerized by the application of heat or by the use of radical-generating catalysts such as benzoyl peroxide, tertiary-butyl hydroperoxide, tertiary butyl perbenzoate, cumene hydroperoxide, cumene diperoxide, diazobisisobutyronitrile, hydrogen peroxide, redox catalyst systems such as tertiarybutyl peroxide in the presence of cobalt naphthenate, etc. They can be readily polymerized or copolymerized also under the influence of ultraviolet light or ionizing radiation from any source, such as X-ray machine, linear accelerators, resonant transformer accelerators, natural and synthetic radioactive material, van der Graaf machines and the like.

The crosslinkable monomers of this invention copolymerize readily with other vinyl or vinylidene monomers containing ethylenic unsaturation, $>C=C<$, typical examples of wich are: styrene, vinyl toluene, tertiary butyl styrene, alpha-methylstyrene, monochlorostyrene, dichlorostyrene, divinylbenzene, ethyl vinyl benzene, diisopropenyl benzene, methyl acrylate, ethyl acrylate, methyl methacrylate, ethyl methacrylate, acrylonitrile, methacrylonitrile, the vinyl esters, such as vinyl acetate, and the monovinyl esters of saturated and unsaturated aliphatic, monobasic and polybasic acids such as the vinyl esters of the following acids: propionic, isobutyric, caproic, oleic, stearic, acrylic, methacrylic, crotonic, succinic, maleic, fumaric, itaconic, hexahydrobenzoic, citric, tartaric, etc., as well as the corresponding allyl, methallyl, etc., esters of the aforementioned acids, the itaconic acid monoesters and diesters, such as the methyl, ethyl, butyl esters, etc.; the maleic and fumaric acid monoesters, diesters and their amide and nitrile compounds, such as diethyl maleate, maleyl tetramethyl diamide, fumaryl dinitrile, dimethyl fumarate, cyanuric acid derivatives having at least one copolymerizable unsaturated group attached directly or indirectly to the triazine ring such as diallyl ethyl cyanurate, triallyl cyanurate, etc.; ethers such as vinyl allyl ether, divinyl ether, diallyl ether, resorcinol divinyl ether, etc.; diallyl chlorendate, diallyl tetrachlorophthalate, diallyl tetrabromophthalate, dibromopropargyl acrylate, as well as the partial fusible or soluble polymerizable polymers of the hereinabove listed monomers, etc.

In preparing the interpolymerization products of the crosslinkable derivatives of this invention, and one or more modifying monomers of the type listed hereinabove, the modifying monomers can constitute as much as 98 to 99 percent by weight of the whole, whereas in other cases the modifying monomers can constitute as little as 1 to 2 percent by weight of the whole; in general, however, the modifying monomer or monomers are used in the range of 20 to 80 percent by weight of the whole.

Where it is desirable to produce the monomer per se it is sometimes desirable to use a polymerization inhibitor to prevent the formation of substantial amounts of polymer during the reaction. Where it is not objectionable to have some polymer or even large amounts of polymer, depending on the reaction temperature and other conditions, the reaction may be conducted in the absence of inhibitor.

The new crosslinkable derivatives of this invention can be used also to modify other polymers such as polyvinylacetate, polymethylmethacrylate, cellulose acetate, cellulose butyrate, ethyl cellulose, polyethylene adipate, polydecamethyl sebacate, polystyrene, polyvinyl chloride, poly-(vinyl chloride-vinyl acetate) copolymers, polyethylene adipamide, polycaprolactam, etc. The new crosslinkable derivatives of this invention are especially useful for modifying polymers containing unsaturated vinyl or vinylidene groups with which they copolymerize readily, such as the natural and synthetic polydienes commonly known as rubbers; partially polymerized fusible, soluble polyallyl esters such as diallyl phthalate, diallyl succinate; linear polymers of allyl acrylate, allyl methacrylate, p-allyloxy-styrene, etc., and particularly the unsaturated alkyd resins, which are well known in the art, such as the maleic, fumaric, itaconic acid esters of polyhydric alcohols which can be modified by other mono- and polycarboxylic acids, for example, ethylene glycol-maleate, ethylene glycol-maleate-phthalate, propylene glycol-maleate-phthalate, propylene glycol-fumarate phthalate, di-(hydroxyethoxy)phenyl-fumarate, di(hydroxypropoxy)phenyl-fumarate, etc. In such modifications 1–80 percent, preferably 5–50 percent of the crosslinkable derivative is desirable.

The compositions of this invention are useful in the preparation of molded, cast, laminated and coated products and as adhesives, impregnants and protective coatings. They can be used alone or with fillers, dyes, pigments, opacifiers, lubricants, plasticizers, natural and synthetic resins or other modifying bodies.

In coating, impregnating and similar applications, the compositions, without added solvent, can be applied to the object to be treated and polymerized, with or without the application of heat and pressure, to form the final insoluble polymeric compositions in situ. These new synthetic materials can be used as impregnants for many porous bodies, such as cork, pottery, felts, or fabricated bodies with interstoces, such as the windings of electrical coils, netted fibers, interwoven cotton or glass materials, etc. They can also be used for the production of wire coatings and winding tapes, and for protectively coating impervious articles, such as metals, or for coating and impregnating articles such as paper, wood cloth, glass fibers in felted, woven or other form, concrete, linoleum, synthetic boards, etc. These new synthetic materials can also be employed in making laminated fibrous sheet materials wherein superimposed layers of cloth, paper, glass fabrics or mats, etc., are firmly bonded together with these new compositions.

For coating or impregnating applications where the presence of a small amount of solvent in the cured composition is not objectionable, the mixed starting component can be diluted with volatile or non-volatile solvents or diluents best suited for the particular service application, and then can be polymerized after the application of the solution to the particular article to be coated or impregnated, or impregnated and coated. By suitable selection of the starting material and the conditions of interpolymerization, interpolymers can be obtained in an insoluble, infusible state practically resistant to the destructive effect of other chemical bodies, such as acid, bases, salts, solvents, swelling agents, and the like.

The polymeric compositions of this invention are particularly useful as coating compositions on all types of substrates, including cellulose in its various forms, such as paper, wood, paper board, wood board, wood pulp, regenerated cellulose in film or fiber form, laminates of the various types including those prepared from fibrous fillers bonded with urea, melamine, epoxy and polyester resins, plaster board, concrete in its various forms such as slabs, blocks and the like. They may also be used as impregnants for porous bodies such as the compositions hereinabove named, as well as for synthetic and natural sponges, etc. Particularly do they find use as bonding agents and adhesives for solid, porous and foamed bodies.

Various methods of practicing the invention are illustrated by the following examples. These examples are intended merely to illustrate the invention and not in any sense to limit the scope of the invention nor the manner in which the invention can be practiced. The parts and percentages recited therein and throughout this specification, unless specifically provided otherwise, refer to parts by weight and percentages by weight.

EXAMPLE I a. A mixture of 168 parts of hexamethylene diisocyanate, 256 parts of glycidyl acrylate and 0.1 part of tetramethylammonium bromide in 3 parts of methanol and 0.1 part of t-butyl catechol are reacted with stirring under a nitrogen atmosphere at 90° C. for 2 hours; the free isocyanate disappears yielding the dioxazolidinone

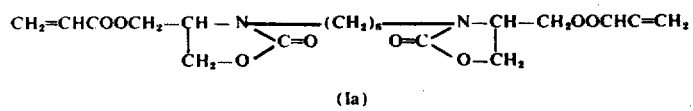

(I)

compound, which on analysis yields values of 56.54% C, 6.66% H and 6.57% N, which are in close agreement with the theoretical calculated values, and which may also contain some of the equivalent isomeric dioxazolidinone compound b. When the procedure of Example I(a) is repeated using 270 parts of glycidyl methacrylate instead of the acrylate, there is obtained the corresponding methacrylate derivative

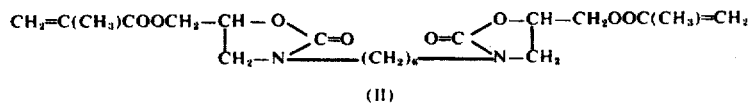

(II)

c. When an equivalent weight of 2-cyanoglycidyl acrylate is used in the procedure of Example I(a) instead of glycidyl acrylate there is obtained the corresponding derivative

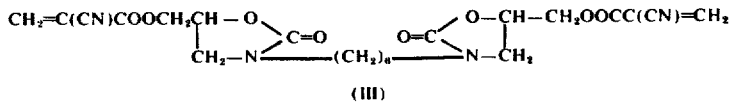

(III)

EXAMPLE II

The procedure of Example I is repeated using glycidyl acrylate and instead of the hexamethylene diisocyanate, the equivalent amount of the polyisocyanate shown in Table I, and there are obtained the polydioxazolidinone derivatives IV and XVI inclusive.

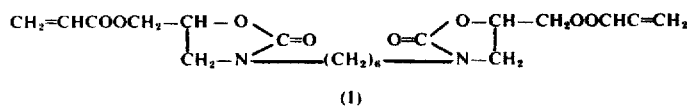

(Ia)

TABLE I

Reaction of Glycidylacrylate with Various Polyisocyanates polydioxazolidinone

| | Polyisocyanate used Q(NCO)$_n$ | Derivative $\left[ O=C {\overset{O-CH-CH_2OOCHC=CH_2}{\underset{N-CH_2}{\diagdown}}} \right]$ | Q | n |
|---|---|---|---|---|
| a) | OCNCH$_2$CH$_2$NCO | IV | —(CH$_2$)$_2$— | 2 |
| b) | OCN(CH$_2$)$_3$NCO | V | —(CH$_2$)$_3$— | 2 |
| c) | OCNC$_6$H$_4$NCO | VI | —C$_6$H$_4$— | 2 |
| d) | OCNC$_6$H$_4$(CH$_3$)NCO | VII | —C$_6$H$_3$(CH$_3$)— | 2 |
| e) | OCNC$_6$H$_4$C$_6$H$_4$NCO | VIII | —(C$_6$H$_4$)$_2$— | 2 |
| f) | OCNC$_6$H$_4$OC$_6$H$_4$NCO | IX | —C$_6$H$_4$OC$_6$H$_4$— | 2 |
| g) | OCNC$_6$Cl$_4$NCO | X | —C$_6$Cl$_4$— | 2 |
| h) | OCNH$_2$CC$_6$H$_4$CH$_2$NCO | XI | —H$_2$CC$_6$H$_4$CH$_2$— | 2 |
| i) | OCNH$_2$CC$_6$H$_{10}$CH$_2$NCO | XII | —H$_2$CC$_6$H$_{10}$CH$_2$— | 2 |
| j) | (CH$_2$OCH$_2$CH$_2$CH$_2$NCO)$_2$ | XIII | [CH$_2$O(CH$_2$)$_3$—]$_2$ | 2 |
| k) | ![structure n''=1] | XIV | H+C$_6$H$_3$CH$_2$+C$_6$H$_4$ | 3 |
| l) | ![structure n''=3] | XV | H+C$_6$H$_3$CH$_2$+C$_6$H$_4$ | 5 |

TABLE I-continued

Reaction of Glycidylacrylate with Various Polyisocyanates

| Polyisocyanate used Q(NCO)$_n$ | Derivative polydioxazolidinone | Q | n |
|---|---|---|---|
| | 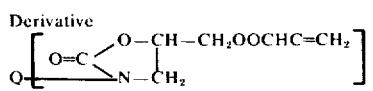 | | |

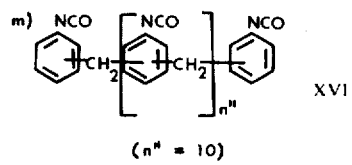 XVI (n″ = 10)

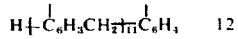 12

EXAMPLE III

The procedure of Example II is repeated using glycidyl methacrylate instead of glycidyl acrylate with the polyisocyanates a) to m) inclusive and there are obtained the methacrylic derivatives XVII to XXIX respectively of the formula

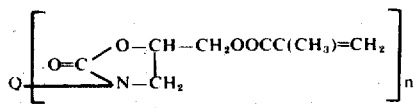

corresponding to the acrylic derivatives IV to XVI respectively.

EXAMPLE IV a. The procedure of Example I is repeated to react a polypropyleneglycol (molecular weight 800) previously end-capped with two moles of tolyl diisocyanate, OCNC$_6$H$_3$(CH$_3$)NHCOO[CH$_2$C(CH$_3$)O]-$_n$OCHNC$_6$H$_3$(CH$_3$)NCO, (molecular weight 1148) with two moles of glycidyl acrylate and there is obtained the corresponding dioxazolidinone derivative.

b. The trimethylolpropane-6 mole propylene oxide adduct end-capped with 3 moles of tolyldiisocyanate (as a triisocyanate) is reacted with 3 moles of glycidyl acrylate by the procedure of Example I, and there is obtained the corresponding tri-oxazolidinone derivative.

c. The pentaerythritol-16 mole ethylene oxide adduct end-capped with 4 moles of tolyldiisocyanate (as a tetraisocyanate) is reacted with 4 moles of glycidyl acrylate by the procedure of Example I and there is obtained the corresponding tetraoxazolidinone derivative.

d. The bisphenol A-2 mole ethylene oxide adduct end-capped with two moles of m-phenylene diisocyanate, OCN—C$_6$H$_4$NHCOOCH$_2$CH$_2$OC$_6$H$_4$C(CH$_3$)$_2$C$_6$-H$_4$OCH$_2$CH$_2$OOCHNC$_6$H$_4$NCO, is reacted by the procedure of Example I twice with (i) glycidyl acrylate and (ii) with glycidyl methacrylate respectively, and there are obtained the corresponding acrylic and methacrylic dioxazolidinone derivatives respectively.

e. The polymeric ethyleneglycol succinate end-capped with hexamethylenediisocyanate, OCN(CH$_2$)$_6$NHCO[OCH$_2$CH$_2$OOCCH$_2$CH$_2$CO]-$_4$OCH$_2$CH$_2$OOCHN(CH$_2$)$_6$NCO, (molecular weight 1014) is reacted by the procedure of Example I with glycidyl acrylate and the corresponding dioxazolidinone derivatives is obtained.

f. The polymeric ethyleneglycol maleate end-capped with tolyl diisocyanate,

OCNC$_6$H$_3$(CH$_3$)NHCOO[OCH$_2$CH$_2$OOCCH=CH-CO]$_3$OCH$_2$CH$_2$OOCHNC$_6$H$_3$(CH$_3$)NCO, (molecular weight 812) is reacted by the procedure of Example I with two moles of glycidyl acrylate and the corresponding dioxazolidinone derivative is obtained.

When two moles of glycidyl methacrylate are used instead of glycidyl acrylate and corresponding methacrylic ester is obtained.

g. The diisocyanate

prepared from two moles of tolyldiisocyanate and one mole of glycidol,

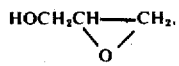

is reacted by the procedure of Example I with (i) glycidyl acrylate; (ii) glycidyl methacrylate; (iii) glycidyl cyanoacrylate, and the corresponding dioxazolidinone derivatives containing terminal acrylate, methacrylate and cyanoacrylate ester functions respectively are obtained.

h. The diisocyanate,

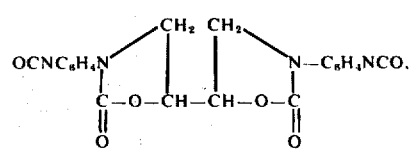

prepared from one mole of butadiene diepoxide and two moles of phenylene diisocyanate, is reacted with two moles of glycidyl acrylate by the procedure of Example 1 to give the dioxazolidinone derivative

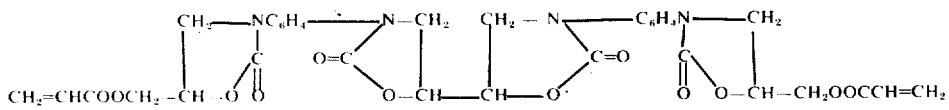

i. The diisocyanate, OCNC₆H₃N=HCC₆H₄CH=NC₆H₃NCO, prepared from one mole of terephthaldehyde and two moles of phenylenediisocyanate, is reacted with two moles of glycidyl acrylate by the procedure of Example 1 to yield the dioxazolidinone derivative

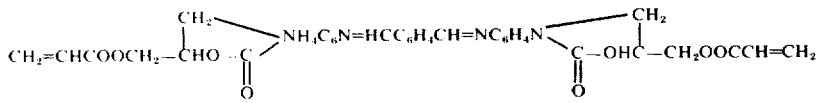

EXAMPLE V

A mixture of 174 parts of tolyldiisocyanate, 256 parts of glycidyl acrylate, 50 parts of styrene and 0.05 parts of tetramethylammonium chloride and 0.05 parts of tert-butyl catechol are reacted under a nitrogen atmosphere at 80°–90° C. for 2 and one-half hours or until the isocyanate disappears, and there is obtained directly a copolymerizable styrene solution of the dioxazolidinone.

When the styrene is replaced by equivalent weights respectively of methyl methacrylate, ethylacrylate, vinyl acetate, monochlorostyrene, dichlorostyrene, diallyl phthalate, diallyl fumarate, divinylbenzene, allyl methacrylate or trimethylene dimethacrylate, respectively, copolymerizable solutions containing the respective monomer and the dioxazolidinone derivative are obtained.

EXAMPLE VI

To 600 parts of methylmethacrylate is added 0.15 part of tert-butyl catechol, 488 parts (1 mole) of ethylene glycol maleate, H[OCH₂CH₂OOCCH=CHCO]₃OCH₂CH₂OH, 344 parts of tolyl diisocyanate (2 moles) and 0.1 part of tetramethylammonium bromide and the mixture reacted under nitrogen at 90° C. for about 1 hour. There is then added 256 parts (2 moles) of glycidyl acrylate, the reaction continued for an addition 1 to 1 and one-half hours, and there is obtained a 50% copolymerizable solution of methyl methacrylate and the dioxazolidinone derivative similar to that of Example IV(f).

EXAMPLE VII

To the polymerizable products of Examples I to VI inclusive is added 0.1% by weight of tertiary butyl perbenzoate and the mixture heated at 80° C. for 24 hours and in all cases insoluble, infusible polymeric castings are obtained. Similar thermoset polymers are obtained when azobisisobutyronitrile, benzoyl peroxide, lauroyl peroxide, tertiary butyl peroxide, cumene hydroperoxide, dicumene peroxide and similar catalysts are used instead of the tertiary butyl perbenzoate.

EXAMPLE VIII

The polymerizable derivatives I to XVI inclusive of Examples I and II are exposed to the beam of a van der Graaf accelerator to a total dosage of 7.5 megarads and insoluble, infusible polymer products are obtained.

Insoluble, infusible polymers are obtained similarly when the drivatives are exposed to ultraviolet radiation of a carbon, mercury or Xenon lamp.

EXAMPLE IX

To a mixture of 75 parts by weight of derivative XIV is added 25 parts of styrene, 40 parts of calcium carbonate as a filler and 1 part of tertiary butyl perbenzoate and the mixture blended to uniformity. The mixture is applied to glass fiber mats (1.5 ounces of glass per square foot of surface) so that the glass comprises about 40 percent of the composition. Five glass mats are arranged one-atop-another as a five-layer laminate assembly and cured between the heated plates of a mold for 15 minutes at 125° C. at 150 psi. The flexural strength of the as-prepared laminate is in the range of 30,000 to 32,000 psi and the tensile strength is in the range of 17,000 to 18,000 psi.

EXAMPLE X

A solution is prepared from 100 parts of dioxazolidinone derivative VII, 100 parts of diallyl phthalate, 50 parts of toluene and 50 parts of ethyl alcohol, and 2 parts of dicumyl peroxide. The solution is applied as a coating to multi-filament glass threads by drawing the fibers through the solution and is then dried to evaporate the toluene and alcohol. The dried impregnated thread is then used for the production of spiral wound filament forms and the formed structure cured at 130° C. for 2 hours, followed by postcuring at 180° C. for 50 hours.

EXAMPLE XI

One mole (172 parts) of tolyldiisocyanate, OCNC₆H₃(CH₃)NCO, and 7 moles (896 parts) of glycidyl acrylate are reacted by the procedure of Example 1 and there is obtained a copolymerizable solution of 428 parts derivative VII in 640 parts of glycidyl acrylate, as a copolymerizable solvent. To a sample of the solution is added 0.25 parts by weight of benzoyl peroxide and the mixture heated at 80° C. for 6 hours, and there is obtained an insoluble, infusible copolymer which shows outstanding adhesion to glass, wood, fiber board, cement and metals such as iron, aluminum, silver, copper and zinc.

Polymers produced from the polymerizable polyoxazolidinone compounds of this invention initially have a plurality of repeating units therein of the formula:

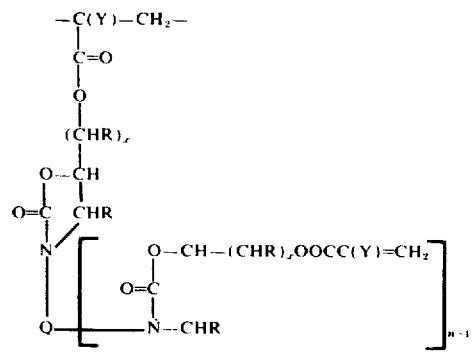

As the polymerization proceeds, crosslinking occurs by reaction of the vinyl groups in the other radicals attached to Q. This crosslinking gives complicated structures difficult to portray by formulas but when $n$ represents only 2, the crosslinking repeating units can be represented by the formula:

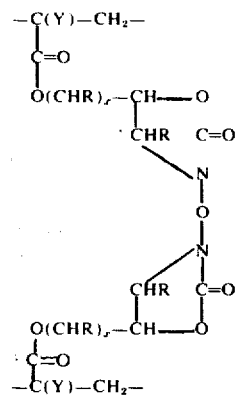

Where $n$ represents 3 or more, the number of polymerized repeating unit groups extending from Q can be increased accordingly.

For example the polymers produced from the polymerizable compound of Example 19(a) has a plurality of repeating units selected from

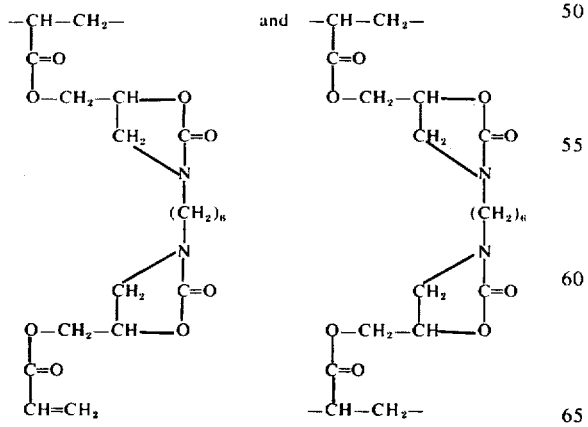

Polymers produced by polymerization of the glycidyl acrylate derivatives of Examples I and II can be represented as having a plurality of repeating units therein selected from the class consisting of

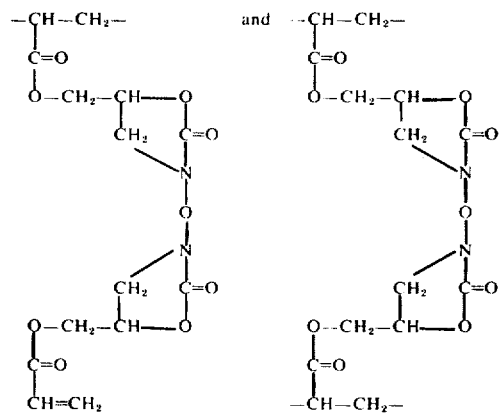

wherein Q represents —$(CH_2)_6$— for the product derived from Example I and for the products from Example II the Q groups are indicated in Table I.

For example, polymers derived from the glycidyl acrylate reaction product of phenylenediisocyanate, identified as VI of Table I, in Example II, have a plurality of repeating units selected from

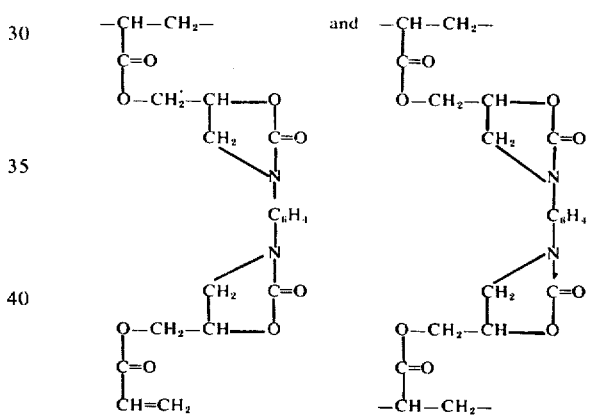

Polymers derived from glycidyl acrylate reaction product of xylenediisocyanate, identified as XI in Table I of Example II, have a plurality of repeating units selected from

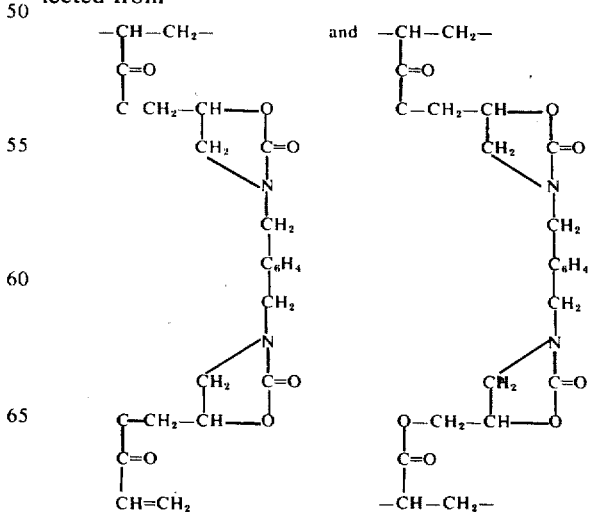

EXAMPLE XII

The procedure of Example I is repeated a number of times using individually an equivalent amount of the diisocyanate compounds listed below in place of the hexamethylene diisocyanate with the derivatives in each case having the formula

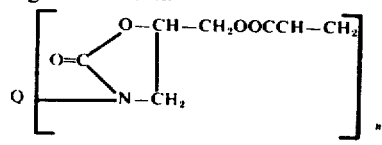

| Polyisocyanate Used Q(NCO)$_n$ | Q | n |
|---|---|---|
| (a) OCHC$_6$H$_2$(CH$_3$)$_2$NCO | —C$_6$H$_2$(CH$_3$)$_2$— | 2 |
| (b) OCNCH$_2$C$_6$H$_4$NCO | —CH$_2$C$_6$H$_4$— | 2 |
| (c) OCNC$_{10}$H$_6$NCO | —C$_{10}$H$_6$— | 2 |
| (d) CH(C$_6$H$_4$NCO)$_3$ | CH(C$_6$H$_4$—)$_3$ | 3 |
| (e) CH$_2$(C$_6$H$_4$NCO)$_2$ | CH$_2$(C$_6$H$_4$—)$_2$ | 2 |
| (f) OCNC$_6$H$_4$OC$_6$H$_4$OC$_6$H$_4$NCO | —C$_6$H$_4$OC$_6$H$_4$OC$_6$H$_4$— | 2 |
| (g) OCNC$_6$H$_4$C(O)C$_6$H$_4$NCO | —C$_6$H$_4$C(O)C$_6$H$_4$— | 2 |
| (h) OCNC$_6$H$_3$(CH$_3$)C(O)OC$_6$H$_3$(CH$_3$)NCO | —C$_6$H$_3$(CH$_3$)C(O)OC$_6$H$_3$(CH$_3$)— | 2 |
| (i) OCNC$_6$H$_2$(CH$_3$)$_2$SC$_6$H$_2$(CH$_3$)$_2$NCO | —C$_6$H$_2$(CH$_3$)$_2$SC$_6$H$_2$(CH$_3$)$_2$— | 2 |
| (j) OCNC$_6$H$_4$SC$_6$H$_4$SC$_6$H$_4$NCO | —C$_6$H$_4$SC$_6$H$_4$SC$_6$H$_4$— | 2 |
| (k) OCN(CH$_2$)$_6$O(CH$_2$)$_6$O(CH$_2$)$_6$NCO | —(CH$_2$)$_6$O(CH$_2$)$_6$O(CH$_2$)$_6$— | 2 |
| (l) OCNC$_{10}$H$_6$SO$_2$C$_{10}$H$_6$NCO | —C$_{10}$H$_6$SO$_2$C$_{10}$H$_6$— | 2 |
| (m) OCN(CH$_2$)$_2$NHC(O)O(CH$_2$)$_2$NCO | —(CH$_2$)$_2$NHC(O)O(CH$_2$)$_2$— | 2 |
| (n) OCNC$_6$H$_4$N=CHC$_6$H$_4$NCO | —C$_6$H$_4$N=CHC$_6$H$_4$— | 2 |

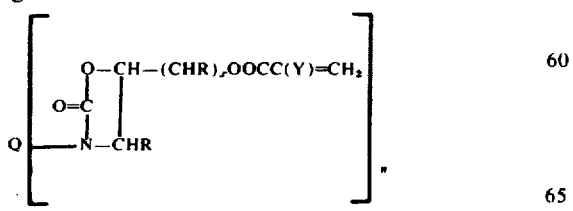

In each case the polydioxazolidinone is obtained having the general formula given above with the Q group being the same as present in the starting polyisocyanate compound. Each of the products is treated according to the procedure of Example VII to give infusible, insoluble polymeric castings.

Many of the polyisocyanates used in preparing the compositions of this invention are available commercially and the others are prepared by standard procedures for preparing isocyanate compounds. Many of these are described in U.S. Pat. Nos. 3,367,992; 3,334,110; 3,415,901; 3,440,230; 3,458,527 as well as other patents and publications.

While certain features of this invention have been described in detail with respect to various embodiments thereof, it will, of course, be apparent that other modifications can be made within the spirit and scope of this invention, and it is not intended to limit the invention to the exact details shown above except insofar as they are defined in the following claims:

The invention claimed is:
1. A polymerizable polyoxazolidinone compound having the formula

$$\left[ \begin{array}{c} \text{O—CH—(CHR)}_x\text{OOCC(Y)=CH}_2 \\ \text{O=C} \\ \text{Q} \quad \text{N—CHR} \end{array} \right]_n$$

wherein

*n* is an integer having a value of at least 2 and no more than 12,

Y represents H, CH$_3$ or CN,

R has no more than 10 carbon atoms and represents hydrogen, or alkyl, cycloalkyl, phenyl, naphthyl, and alkylated phenyl in which the total number of carbon atoms in the alkyl groups does not exceed 4, except that in the (CHR)$_x$ no more than one R represents anything other than hydrogen,

*x* is an integer having a value of 1 to 8, and

Q is a polyvalent organic moiety of 2–83 carbon atoms consisting of alkylene, phenylene, xylylene, tolylene, naphthylene, diphenylene, CH(C$_6$H$_4$—)$_3$, CH$_2$(C$_6$H$_4$—)$_2$, or chloro derivatives thereof in which the chlorine atoms are attached directly to an aromatic nucleus, or —Q'ZQ'— wherein Z is the divalent —O—, —O—Q'—O—, —C(O)—, —C(O)O—, —S—, —S—Q'—S—, —SO$_2$—, —NHC(O)O—, or

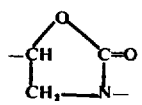

and Q' is phenylene, tolylene, xylylene, naphthylene or alkylene of 2–20 carbon atoms;

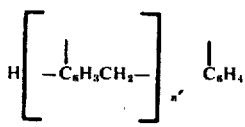

wherein *n'* is 2–12;

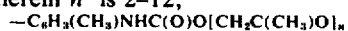

(O)CNHC$_6$H$_3$(CH$_3$)— wherein *n* is 2–12;

C$_3$H$_5$O$_3$[—CH(CH$_3$)CH$_2$OCH(CH$_3$)CH$_2$—]$_3$;

Cl—CH$_2$O(CH$_2$CH$_2$O)$_4$—]$_4$;

C(CH$_3$)$_2$[C$_6$H$_6$OCH$_2$CH$_2$OOCNHC$_6$H$_4$—]$_2$;

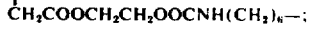

—C₆H₃(CH₃(CH₃)NHC(O)[OCH₂C-
H₂O(O)CCH=CHC(O)]₃OCH₂CH₂(O)OCNHC₆-
H₃—(CH₃);

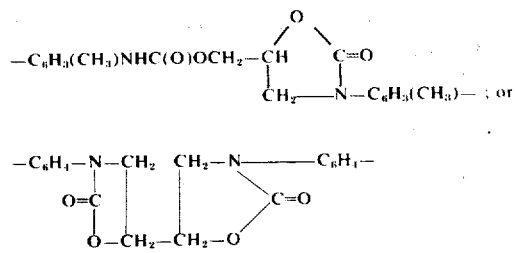

2. The compound of claim 1 in which both R's are hydrogen.
3. The compound of claim 2 in which Y is hydrogen.
4. The compound of claim 2 in which Y is methyl.
5. The compound of claim 2 in which Q is hydrocarbon of 2-20 carbon atoms.
6. The compound of claim 5 in which Y is hydrogen.
7. The compound of claim 5 in which Y is methyl.
8. The compound of claim 5 in which Q is —C₆H₄—.
9. The compound of claim 5 in which Q is —(CH₂)₆—.
10. The compound of claim 5 in which Q is —C₆H₃(CH₃)—.

* * * * *